(12) United States Patent
Dalla Ricca et al.

(10) Patent No.: US 9,956,430 B2
(45) Date of Patent: May 1, 2018

(54) REMOTE CONTROL SYSTEM AND METHOD

(71) Applicant: VARIAN MEDICAL SYSTEMS, INC., Palo Alto, CA (US)

(72) Inventors: Paolo Dalla Ricca, Fremont, CA (US); Kevin Greenberg, San Jose, CA (US)

(73) Assignee: VARIAN MEDICAL SYSTEMS, INC., Palo Alto, CA (US)

(*) Notice: Subject to any disclaimer, the term of this patent is extended or adjusted under 35 U.S.C. 154(b) by 479 days.

(21) Appl. No.: 14/373,036

(22) PCT Filed: Jan. 25, 2013

(86) PCT No.: PCT/US2013/023318
§ 371 (c)(1),
(2) Date: Jul. 18, 2014

(87) PCT Pub. No.: WO2013/112954
PCT Pub. Date: Aug. 1, 2013

(65) Prior Publication Data
US 2014/0371512 A1 Dec. 18, 2014

Related U.S. Application Data

(60) Provisional application No. 61/590,784, filed on Jan. 25, 2012.

(51) Int. Cl.
*A61N 5/10* (2006.01)
*G06F 19/00* (2011.01)

(52) U.S. Cl.
CPC ......... *A61N 5/1064* (2013.01); *A61N 5/1048* (2013.01); *A61N 2005/109* (2013.01);
(Continued)

(58) Field of Classification Search
CPC ............... A61N 5/1064; A61N 5/1048; A61N 2005/1074; A61N 2005/109;
(Continued)

(56) References Cited

U.S. PATENT DOCUMENTS 5,068,820 A * 11/1991 Nojima ............... G06F 13/4226
713/502
6,061,757 A 5/2000 Arimilli et al.
(Continued)

OTHER PUBLICATIONS

Notification of Transmittal of the International Search Report and the Written Opinion of the International Searching Authority, International Application No. PCT/US13/23318, Apr. 15, 2013.

*Primary Examiner* — Michael Maskulinski
*Assistant Examiner* — Anthony J Amoroso
(74) *Attorney, Agent, or Firm* — SU IP Consulting (57) ABSTRACT

A remote control system is configured to support communication between a first environment having a first neutron radiation level and a second environment having a second neutron radiation level includes a first computing device and a second computing device. The first computing device is configured to control a treatment system in the first environment. The second computing device is configured to issue commands in the second environment for the treatment system. The first computing device is further configured to determine whether to enable or disable a function supported by the treatment system, determine whether there is pending time-sensitive data to transmit, and periodically transmit a first radiation therapy data collected in the first environment and a first interrupt to the second computing device in a servo loop.

22 Claims, 8 Drawing Sheets

(52) U.S. Cl.
CPC ............... *A61N 2005/1074* (2013.01); *A61N 2005/1094* (2013.01); *G06F 19/3418* (2013.01)

(58) Field of Classification Search
CPC ........ A61N 2005/1094; G06F 19/3418; G06F 19/34; G06F 19/3406; G06F 2201/00; G06F 2201/855; G06F 2201/87; G06F 2201/875
See application file for complete search history.

(56) References Cited

U.S. PATENT DOCUMENTS

| | | | |
|---|---|---|---|
| 6,118,847 A * | 9/2000 | Hernandez-Guerra | A61B 6/541 250/505.1 |
| 7,680,880 B2 * | 3/2010 | Landfield | H04L 63/1441 370/254 |
| 7,978,062 B2 * | 7/2011 | LaLonde | A61N 1/37282 340/539.1 |
| 2006/0074381 A1 * | 4/2006 | Malave | A61M 5/14248 604/93.01 |
| 2007/0041498 A1 * | 2/2007 | Olivera | A61N 5/103 378/65 |
| 2008/0021741 A1 * | 1/2008 | Holla | G06F 19/321 705/3 |
| 2008/0150754 A1 | 6/2008 | Quendt | |

\* cited by examiner

REMOTE CONTROL SYSTEM AND METHOD

CROSS-REFERENCE TO RELATED APPLICATION

The present application is a U.S. National Stage filing under 35 U.S.C. § 371 of International Application No. PCT/US2013/023318, filed on Jan. 25, 2013, entitled "REMOTE CONTROL SYSTEM AND METHOD." The International Application, including any appendices or attachments thereof, is hereby incorporated by reference in its entirety.

BACKGROUND

Unless otherwise indicated herein, the approaches described in this section are not prior art to the claims in this application and are not admitted to be prior art by inclusion in this section.

A radiotherapy system includes multiple electronic components that are configured to control system parameters, for example, axis motion, beam generation, and power distribution. The electronic components are usually located adjacent to the elements that they control to minimize the number of cables routed through the radiotherapy system or the amount of noise picked up that may occur in long cables.

Such an arrangement (i.e., the electronic components located adjacent to the elements that they control) becomes an issue when the radiotherapy system is configured to deliver a relatively high energy radiation (e.g., above 12 MV). At this energy level, neutrons are generated, and they may interact with the electronic components. Such interactions may create internal transients that cause bit flips. For microprocessors, the effect of such bit flips is significant and undesirable.

In addition, unlike existing systems in other high neutron flux industries (e.g., military and aerospace), a radiotherapy system is normally located less than a few tens of meters from a location having normal neutron levels. Thus, the existing systems are inadequate to address at least the challenges that are associated with the close proximity between such a normal flux area (also sometimes referred to as a console area) and the radiotherapy system.

SUMMARY

In at least some embodiments of the present disclosure, a remote control system configured to support communication between a first environment having a first neutron radiation level and a second environment having a second neutron radiation level includes a first computing device and a second computing device. The first computing device is configured to control a treatment system in the first environment. The second computing device is configured to issue commands in the second environment for the treatment system. The first computing device is further configured to determine whether to enable or disable a function supported by the treatment system, determine whether there is pending time-sensitive data to transmit, and periodically transmit a first radiation therapy data collected in the first environment and a first interrupt to the second computing device in a servo loop.

In at least some other embodiments of the present disclosure, a remote control system configured to support communication between a first environment having a first neutron radiation level and a second environment having a second neutron radiation level includes a first computing device and a second computing device. The first computing device is configured to control a treatment system in the first environment and the second computing device is configured to issue commands in the second environment for the treatment system. The second computing device is further configured to determine whether to issue a command to the first computing device to enable or disable a first function supported by the treatment system, determine whether there is pending time-sensitive data to transmit, and perform a second function in response to a first interrupt asserted by the first computing device and based on a first radiation therapy data received from the first computing device.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Figure 1:
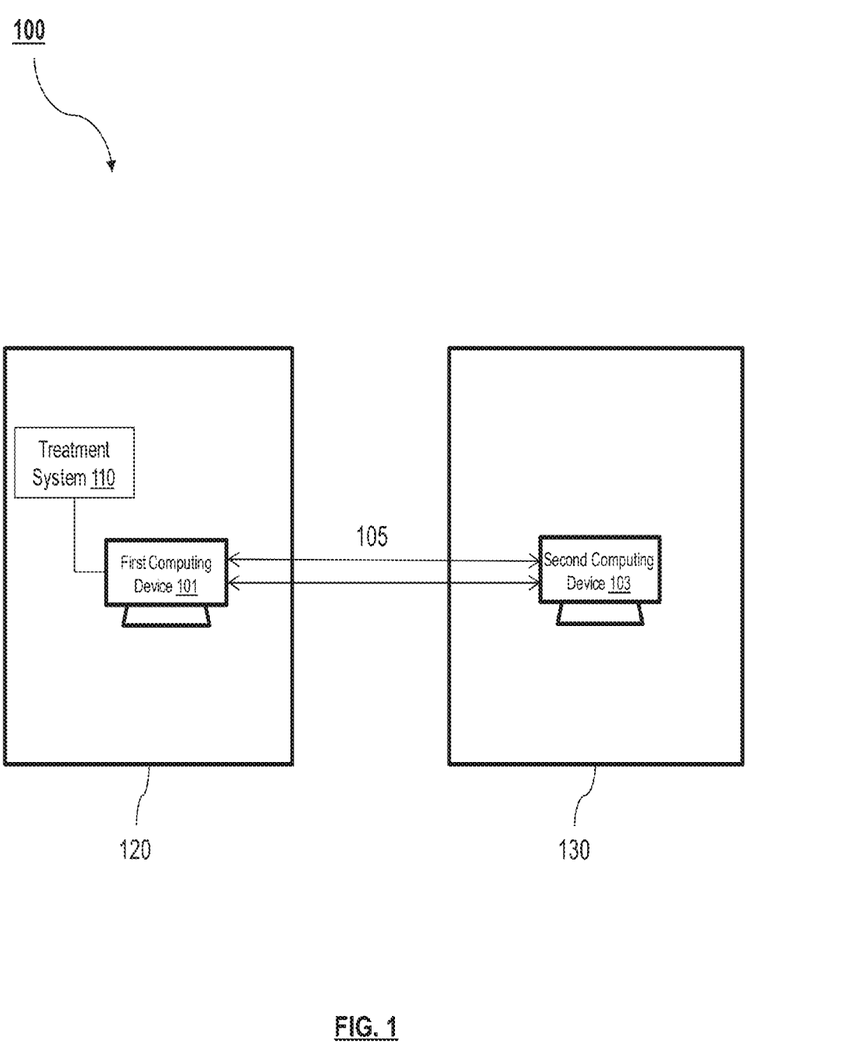
FIG. 1 is an illustrative remote control system.

FIG. 1 is an illustrative embodiment of a remote control system 100 in accordance with some embodiments of the present disclosure. The remote control system 100 includes a first computing device 101 coupled to a treatment system 110 and a second computing device 103. The second computing device 103 may include data processing components, such as processors (e.g., Embedded Technology eXtended (ETX), microblaze, etc.) and field-programmable gate arrays (FPGAs), on one or more printed circuit boards (PCBs) to communicate and/or manage the treatment system 110 via the first computing device 101. Similarly, the first computing device 101 may also include FPGAs, some of which may be flash-based and less sensitive to neutrons, on one or more PCBs to interact with one or more components of the treatment system 110. In some embodiments, the first computing device 101 and the treatment system 110 are located in a first environment 120, and the second computing device 103 is located in a second environment 130. The first environment 120 has a first neutron radiation level, and the second environment 130 has a second neutron radiation level. In some embodiments, the first neutron radiation level is significantly higher than the second neutron radiation level, and the first environment 120 is in close proximity with the second environment 130 (e.g., less than 25 meters apart).

Throughout this disclosure, the first environment 120 is also referred to as a treatment area/room, and the aforementioned PCBs inside the first environment 120 are also referred to as controller boards or controller PCBs. The second environment 130 is also referred to as a console area, and the aforementioned PCBs in the second environment 130 are also referred to as node carrier boards or node PCBs. In some embodiments, a controller board may host a Mezzanine board to communicate with a node carrier board. A Mezzanine board usually has a smaller PCB footprint than a controller board.

The first computing device 101 may be configured to transmit data collected by the treatment system 110 to the second computing device 103. The data may include radiation therapy data associated with the treatment system 110, such as, without limitation, position information, dosage information, and others. In response to the received data, the second computing device 103 may be configured to issue and send a control command, such as a motor drive command, a dosage delivery command, or other commands, for the treatment system 110 to the first computing device 101. The first computing device 101 may be further configured to control the treatment system 110 according to the control command received from the second computing device 103.

In some embodiments, the first computing device 101 is configured to communicate with the second computing device 103 via a communication link 105. An example link may include, without limitation, a high speed serial bus. The communication infrastructure supported by the remote control system 100 provides at least the following capabilities: multiple Ethernet (or modified Ethernet protocol) links between the node and controller PCBs, a mirrored data transfer mode that includes time-critical and non-time-critical data transfer, watchdog, interrupt, interlock, and loop control.

The first computing device 101 and the second computing device 103 may support at least two types of data transfer between them based on the priority of the data. Such data transfer is bidirectional, i.e., from the first computing device 101 to the second computing device 103 or from the second computing device 103 to the first computing device 101. For example, non time-sensitive data may be transmitted with a lower priority. In some embodiments, non time-sensitive data is stored in a set of predetermined registers/ports/memory areas. The set of predetermined registers/ports/memory areas are looped over repeatedly so that the data stored therein is being sent repeatedly as well. The data stored in this set of predetermined registers/ports/memory areas and sent in matter described above may also be referred to as "refresh data." When a part of the non time-sensitive data fails to reach its destination because of a transmission error, the part of the non time-sensitive data may be resent later. Latency exists for the non time-sensitive data transmission because of the looping approach.

Time-sensitive data may be transmitted with a higher priority. For example, the address of a register/port/memory area which stores time-sensitive data may be written in a first-in, first-out (FIFO) manner. The first computing device 101 and the second computing device 103 may have their own FIFO buffers and may be configured to monitor the buffers. If an entry is found in a FIFO buffer at the first computing device 101, the first computing device 101 is configured to access time-sensitive data from the register/port pointed by the entry and transmit the time-sensitive data to the second computing device 103. Similarly, if an entry is found in a FIFO buffer at the second computing device 103, the second computing device 103 is configured to access time-sensitive data from the register/port/memory area pointed to by the entry and transmit the time-sensitive data to the first computing device 101. In the FIFO approach set forth above, time-sensitive data is transmitted once. In some embodiments, time-sensitive data may be retransmitted if such time-sensitive data happens to be stored within the range of the set of predetermined registers/ports/memory area where non time-sensitive data is designated to be stored. For example, the first computing device 101 and the second computing device 103 may each include a refresh watchdog, which may be configured to monitor the predetermined addresses associated with the register/port/memory area. When the predetermined addresses are not updated in a predetermined amount time, the refresh watchdog times out, and the block of data stored in this set of predetermined addresses, including non time-sensitive data and time-sensitive data, may be transmitted (either from the first computing device 101 to the second computing device 103 or from the second computing device 103 to the first computing device 101).

In some other embodiments, time-sensitive data may be retransmitted in response to a retransmission request from its destination if the destination does not receive expected time-sensitive data in time. For example, the first computing device 101 and the second computing device 103 may each include one or more watchdogs other than the refresh watchdog discussed above. These watchdogs may be configured to look for certain expected information, such as, without limititation, interlock data, interrupt, time-sensitive data, and others, within a specified amount of time. When the watchdog times out and the expected information is not received, the first computing device 101 or the second computing device 103 may send a retransmission request to the other side.

Suppose the first computing device 101 is configured to support a motor controlling board in a servomechanism (also referred to as a servo). Some example time-sensitive data may include position information (from the first computing device 101 to the second computing device 103) and motor drive commands (from the second computing device 103 to the first computing device 101). If the first computing device 101 is configured to support a dose related board also in a servo, then some example time-sensitive data may include measured dosage information (from the first computing device 101 to the second computing device 103) and dose delivery commands (from the second computing device 103 to the first computing device 101).

In some embodiments, a plurality of independent communication links are established between the first computing device 101 and the second computing device 103. A first link may have a mirrored architecture with a second link. With the mirrored architecture, any of the two sides of a link may be configured to operate on its own resources (e.g., memory space, registers, etc.) This architecture may also allow a large amount of data on both sides of a link to be transmitted bidirectionally, with each side of the link operating, for much of the data involved, independently. Alternatively, in a master/slave approach, the second computing device 103 may be the master and may be configured to control the data transfer to and from the first computing device 101, the slave. When the master requests data from the slave, the master may wait for two link times for the data to arrive, including the time to send a request to the slave first and the time to wait for the data from the slave.

Figure 2:
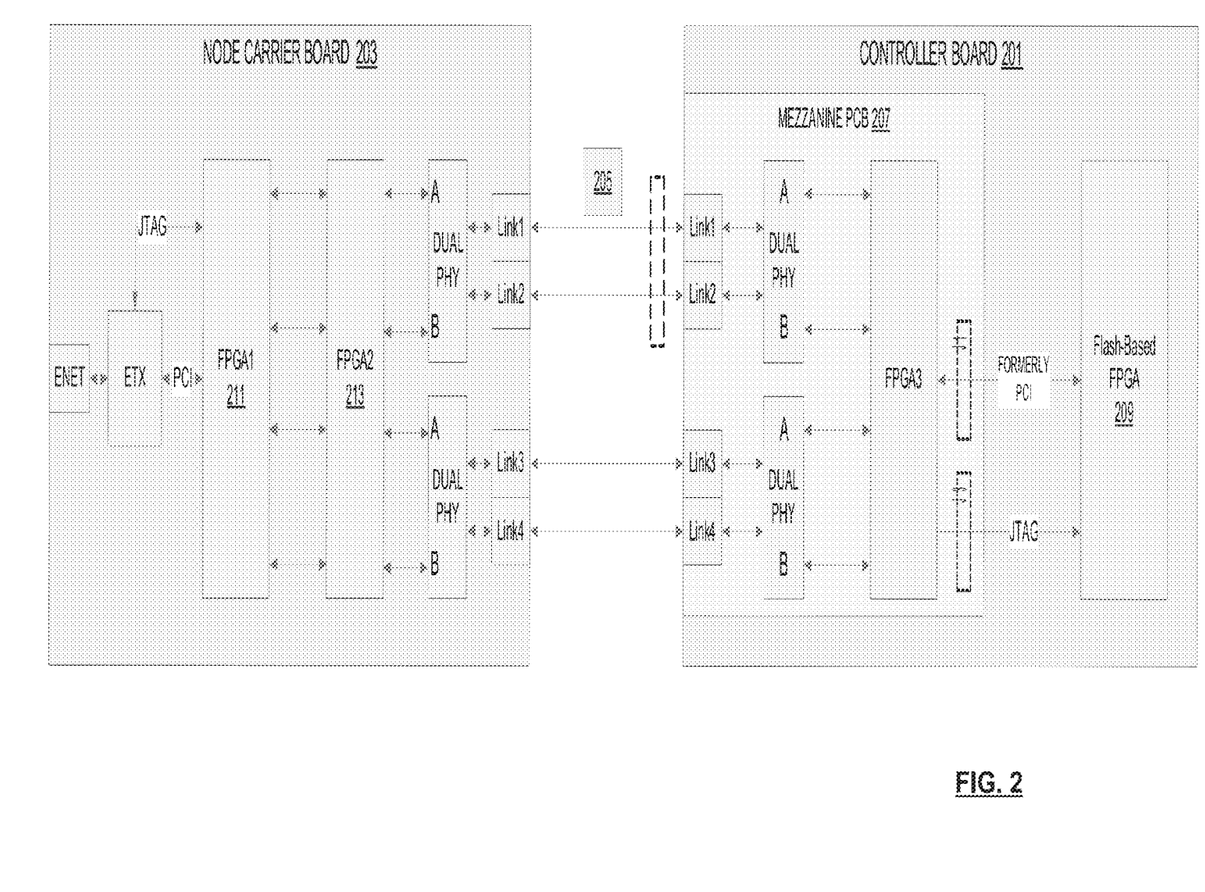
FIG. 2 is a block diagram illustrating certain elements of a node carrier board and a controller board configured for a component of a treatment system.

FIG. 2 is a block diagram illustrating certain elements of a node carrier board 203 and a controller board 201 configured for a component of the treatment system 110 (e.g., the collimator) in accordance with some embodiments of the present disclosure. In conjunction with FIG. 1, the controller board 201 may reside in the first computing device 101, and the node carrier board 203 may reside in the second computing device 103. The controller board 201 and the node carrier board are connected to a plurality of full duplex links, such as links 205. In some embodiments, the links 205 may support the Ethernet protocol or a modified version of the protocol. The links 205 may also support mirrored data transfer capability. As shown, the controller board 201 includes a Mezzanine PCB 207, which includes logic to transmit and receive data to and from the node carrier board 203. In alternative embodiments, the functionality supported by the Mezzanine PCB 207 may be implemented in the controller board 201.

In some embodiments, the controller board 201 includes a flash-based FPGA 209, which may be less sensitive to neutrons. The flash-based FPGA 209 may be configured to support triple modular redundancy (TMR), where storage registers in the FPGA may be tripled, and a voting system may be implemented to utilize the majority of the register states to generate an output, thereby being resistant to bit-flips. In other words, if any one of the three sets of register states fails, the other two sets may correct and mask the fault. The flash-based FPGA 209 may also be configured to support at least interlock mechanisms (e.g., interlock controller(s) and registers), interrupt mechanisms (e.g., interrupt controller(s) and registers), watchdog timers, and error detection and/or correction mechanisms.

In some embodiments, the node PCB 203 includes two FPGAs, 211 and 213. Each of these FPGAs, similar to the flash-based FPAG 209, may also be configured to support at least interlock mechanisms (e.g., interlock controller(s) and registers), interrupt mechanisms (e.g., interrupt controller(s) and registers), watchdog timers, and error detection and/or correction mechanisms. Additional details regarding the interlock mechanisms are further described in conjunction with FIG. 8.

Figure 3:
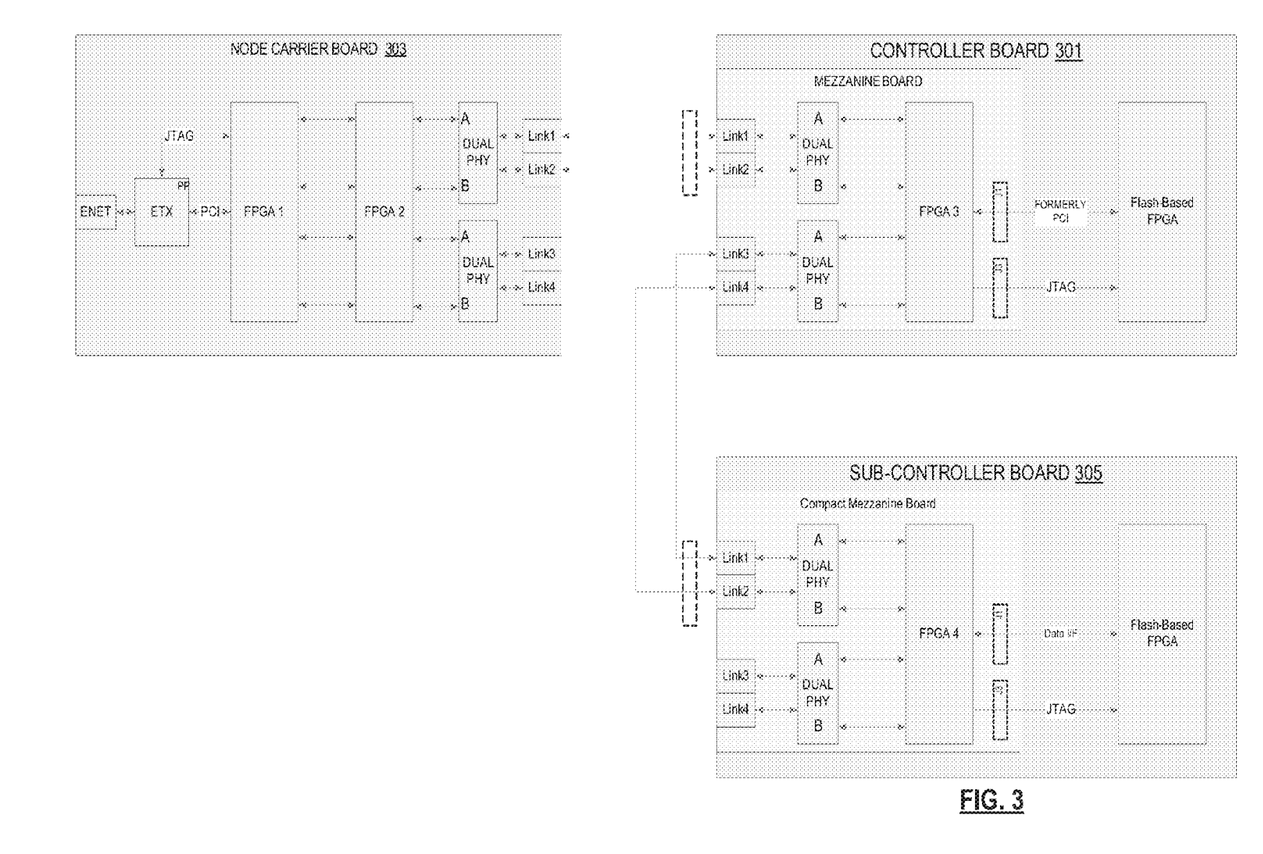
FIG. 3 is a block diagram illustrating certain elements of a node carrier board and a controller board configured for another component of a treatment system and the link to a sub-controller board.

FIG. 3 is a block diagram illustrating certain elements of a node carrier board 303 and a controller board 301 configured for another component of the treatment system 110 (e.g., the Beam Generation and Monitoring (BGM) component) and the link to a sub-controller board 305 (e.g., the BGM-Positioning (BGM-POS) component for motor control of axes needed for generating beams) in accordance with some embodiments of the present disclosure. In some embodiments, the flash-based FPGAs of the controller board 301 and the sub-controller board 305 may be configured to support the similar functions as the flash-based FPGA 209 of FIG. 2, and the FPGAs of the node carrier board 303 may be configured to support the similar function as the FPGAs 211 and 213 of FIG. 2.

Figure 4:
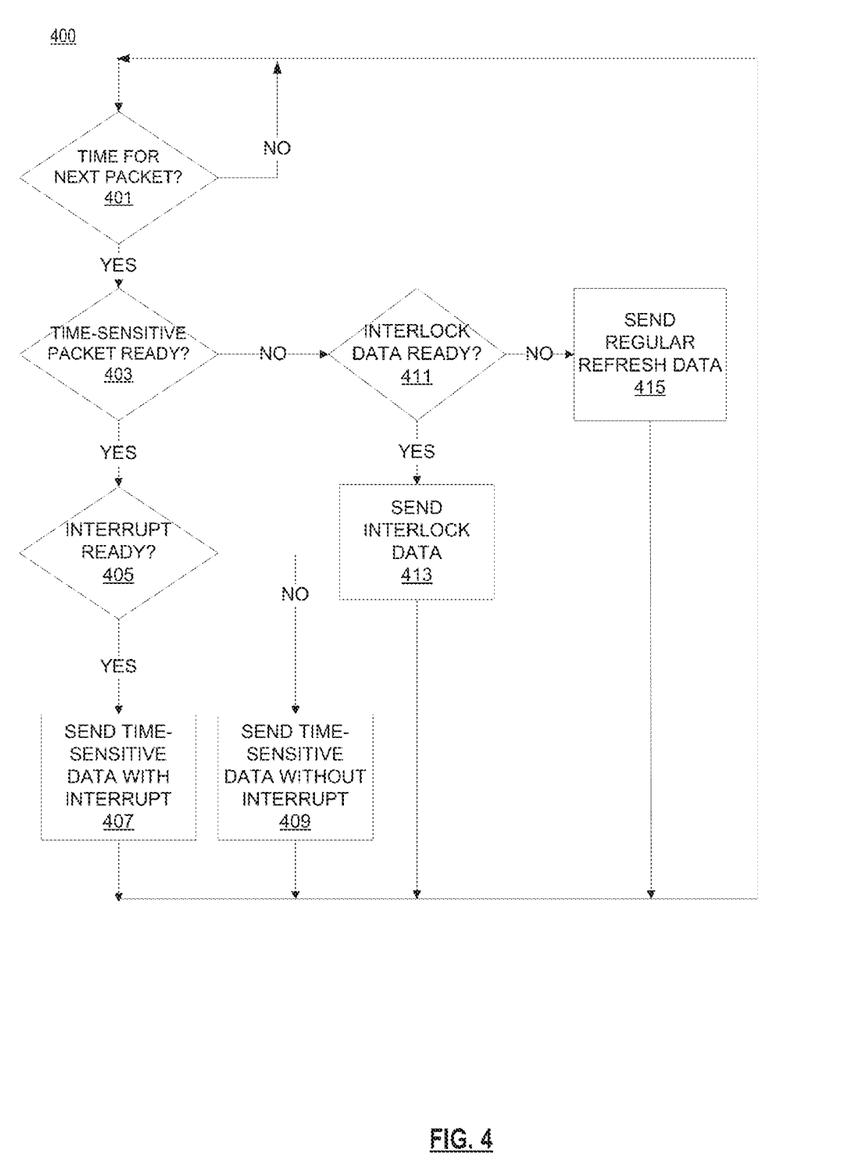
FIGS. 4-5 are flow charts of methods for operating a remote control system from the perspective of a device including a controller board.
Figure 5:
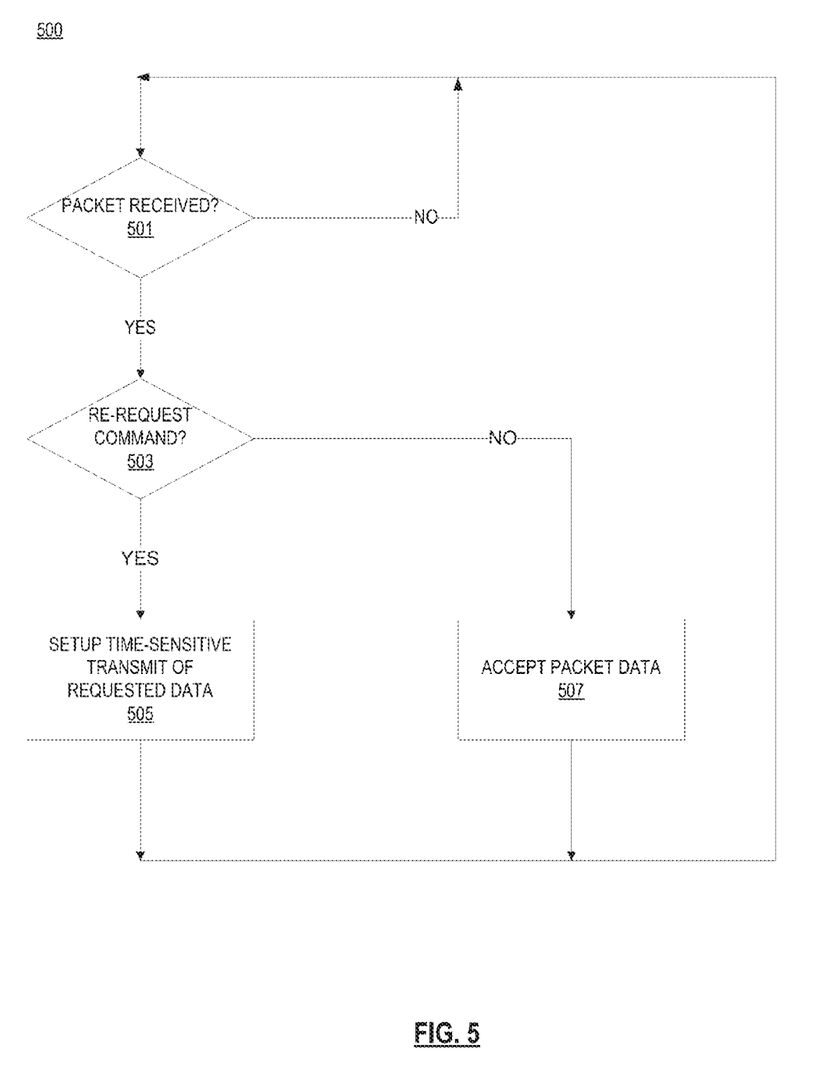

FIGS. 4 and 5 are flow charts of methods for operating a remote control system, such as the remote control system 100, from the perspective of a device including a controller board in accordance with some embodiments of the present disclosure. Method 400 may include one or more operations, functions or actions as illustrated by one or more of blocks 401, 403, 405, 407, 409, 411, 413, and/or 415. Method 500 may include one or more operations, functions or actions as illustrated by one or more blocks 501, 503, 505, and/or 507. The various blocks may be combined into fewer blocks, divided into additional blocks, and/or eliminated based upon the desired implementation. As set forth above, the controller board is configured to transmit information to a node carrier board and receive a command from the node carrier board.

FIG. 4 is a flow chart of the method 400 from the transmission perspective of the device including the controller board, such as the first computing device 101 of FIG. 1, the controller board 201 of FIG. 2, or the controller board 301 of FIG. 3. In conjunction with FIG. 1, processing for method 400 may begin at block 401, "TIME FOR NEXT PACKET?" The first computing device 101 is configured to capture data collected by the treatment system 110, and in some embodiments, is configured to check periodically for this next packet of collected data. If it is time to transmit the next packet of collected data, block 401 may be followed by block 403, "TIME-SENSITIVE PACKET READY?", where the first computing device 101 is configured to analyze the collected data such as whether the collected data may be time-sensitive. For example, the controller board in the first computing device 101 may check its FIFO and service the data in the FIFO as time-sensitive data. If the time-sensitive packet is indeed ready, block 403 may be followed by block 405, "INTERRUPT READY?" If so, then block 405 may be followed by block 407, "SEND TIME-SENSITIVE DATA WITH INTERRUPT," or otherwise followed by block 409, "SEND TIME-SENSITIVE DATA WITHOUT INTERRUPT." In some embodiments, the first computing device 101 is configured to send such time-sensitive data to the second computing device 103 with a higher priority.

If the time-sensitive packet is not ready as determined in block 403, then block 403 may be followed by block 411, "INTERLOCK DATA READY?" If the interlock data is ready, then block 411 may be followed by block 413, "SEND INTERLOCK DATA." Otherwise, block 411 may be followed by block 415, "SEND REGULAR REFRESH DATA." In some embodiments, if the collected data is associated with enabling/disabling a function supported by the treatment system 110, the first computing device 101 may be configured to assert an interlock. The interlock data may be associated with time-sensitive data or non time-sensitive data and may be transmitted along with the collected data to the second computing device 103 for further processing.

FIG. 5 is a flow chart of the method 500 from the receiving perspective of the device including the controller board, such as the first computing device 101 of FIG. 1, the controller board 201 of FIG. 2, or the controller board 301 of FIG. 3. In conjunction with FIG. 1, after transmitting the collected data and/or an interrupt to the second computing device 103, the first computing device 101 is configured to receive a command from the second computing device 103 in response to the collected data and/or the interrupt. Based on the received command, the first computing device 101 is configured to control the treatment system 110 accordingly. The first computing device 101 may be configured to control the treatment system 110 to perform one or more functions. The functions of the treatment system 110 may include power, axis movement, radiation beam configuration, and dosage measurement and delivery.

After transmitting the collected data and/or an interlock to the second computing device 103, the first computing device 101 is configured to receive a command from the second computing device 103 to enable/disable a function of the treatment system 110. Processing for method 500 may begin at block 501, "PACKET RECEIVED?" If packet is indeed received, block 501 may be followed by block 503, "RE-REQUEST COMMAND?" If the received command is not a re-request command, then block 503 may be followed by block 507, "ACCEPT PACKET DATA." For example, based on the received command, the first computing device 101 may be configured to enable or disable one of the power, axis movement, and radiation beam configuration functions of the treatment system 110. On other hand, if the received command is a re-request command, then block 503 may be followed by block 505, "SETUP TIME-SENSITIVE TRANSMIT OF REQUESTED DATA," so that the data being re-requested may be sent as time-sensitive data and assigned a higher priority.

To enhance the fault tolerance of the remote control system 100, in some embodiments, watchdog mechanisms may be employed in the controller board of the first computing device 101. For instance, one watchdog mechanism for the controller board may be configured to check whether a command expected to be received from the second computing device 103 is indeed received within a certain amount of time. If the expected command is somehow not received, then the watchdog times out, and the controller board may be configured to send a time-sensitive message to the second computing device 103 with an interrupt to request for a resend of the command.

Figure 6:
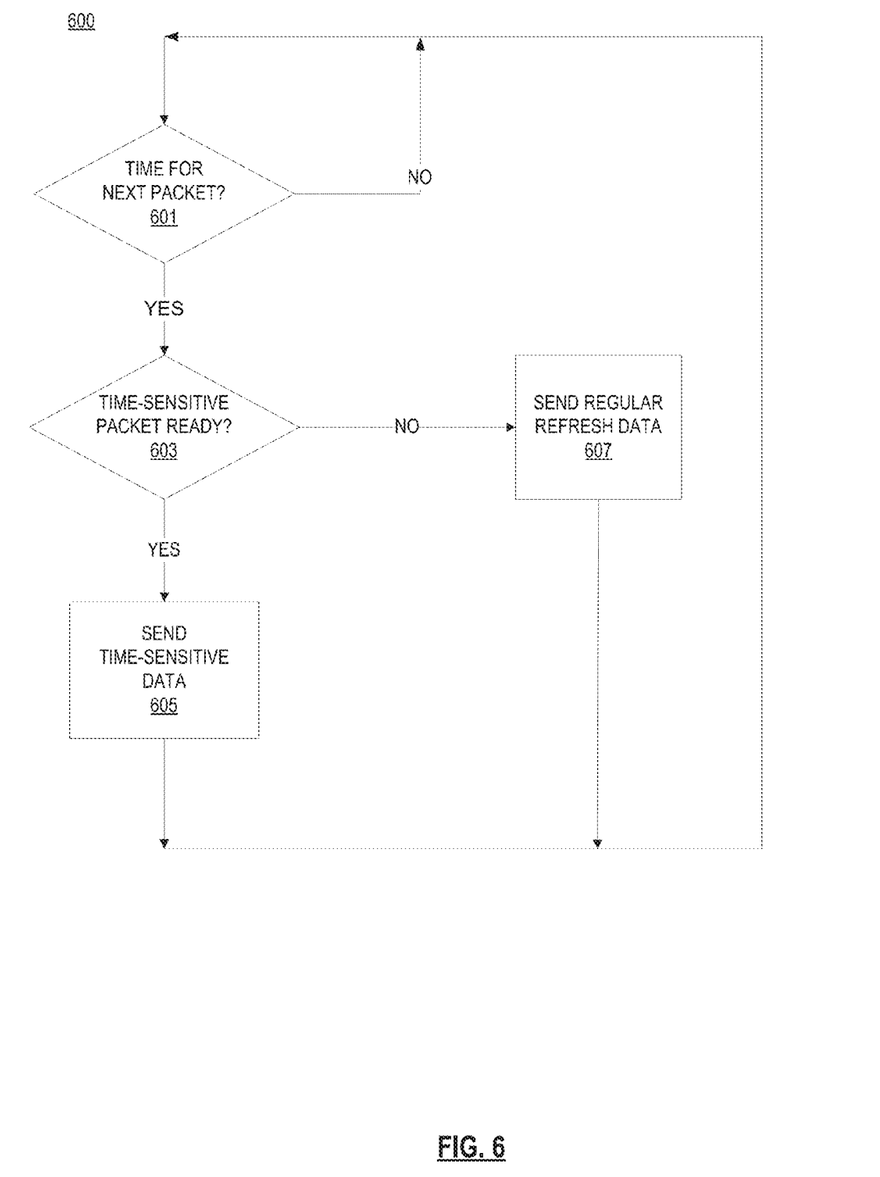
FIGS. 6-7 are flow charts of methods for operating a remote control system from the perspective of a device including a node carrier board.
Figure 7:
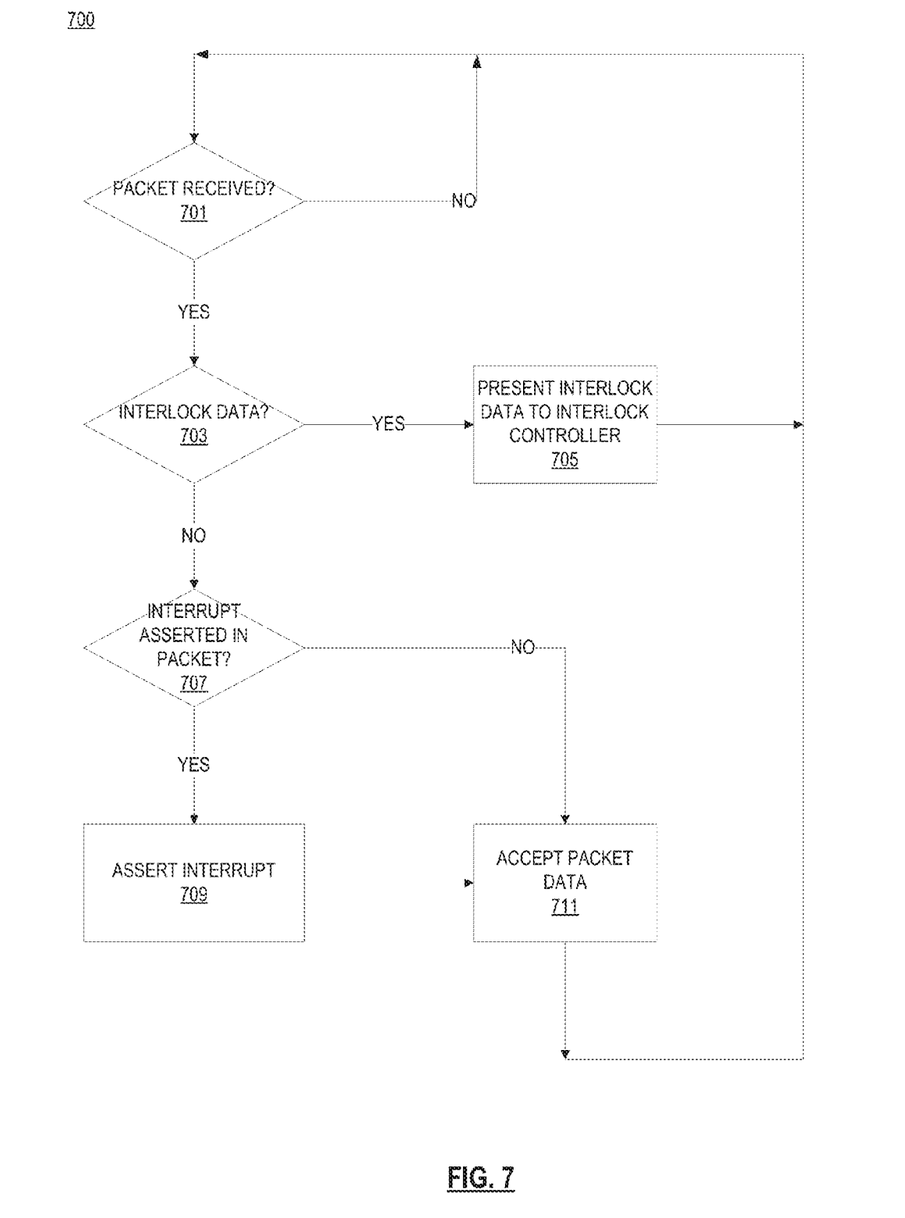

FIGS. 6 and 7 are flow charts of method for operating a remote control system, such as the remote control system 100, from the perspective of a device including a node carrier board in accordance with some embodiments of the present disclosure. Method 600 may include one or more operations, functions or actions as illustrated by one or more of blocks 601, 603, 605, and/or 607. Method 700 may include one or more operations, functions or actions as illustrated by one or more blocks 701, 703, 705, 707, 709, and/or 711. The various blocks may be combined into fewer blocks, divided into additional blocks, and/or eliminated based upon the desired implementation. As set forth above, the node carrier board is configured to issue a command to the controller board in response to the data collected by the node carrier board.

FIG. 6 is a flow chart of method 600 from the transmission perspective of the device including the carrier board, such as second computing device 103 of FIG. 1, the node carrier board 203 of FIG. 2, or the node carrier board 303 of FIG. 3. In conjunction with FIG. 1, processing for method 600 may begin at block 601, "TIME FOR NEXT PACKET?" In some embodiments, the second computing device 103 may be configured to send commands to the first computing device 101. When it is time to send the next packet, block 601 may be followed by block 603, "TIME-SENSITIVE PACKET READY?" If the time-sensitive packet is ready to be sent, then block 603 may be followed by block 605, "SEND TIME-SENSITIVE DATA," where the data sent to the first computing device 101 is assigned a higher priority. On the other hand, if the time-sensitive packet is not ready to be sent, then block 603 may be followed by block 607, "SEND REGULAR REFRESH DATA."

FIG. 7 is a flow chart of method 700 from the receiving perspective of the device including the carrier board, such as second computing device 103 of FIG. 1, the node carrier board 203 of FIG. 2, or the node carrier board 303 of FIG. 3. In conjunction with FIG. 1, processing for method 700 may begin at block 701, "PACKET RECEIVED?" The second computing device 103 may be configured to receive information from the first computing device 101. The information may include data collected from the treatment system 110, an interrupt asserted by the first computing device 101, or an interlock also asserted by the first computing device 101. If packet is received, then block 701 may be followed by block 703, "INTERLOCK DATA?" If the received data is interlock data, then block 703 may be followed by block 705, "PRESENT INTERLOCK DATA TO INTERLOCK CONTROLLER," where the interlock controller of the second computing device 103 may be configured to process the interlock data. For example, the interlock controller may overwrite the asserted interlock under one set of settings or issue a command to enable/disable some functionalities of the treatment system 110 under another set of settings. In some embodiments, such a command to enable/disable functionalities of the treatment system 110 may be considered time-sensitive and may be sent with a high priority.

If the received data is not interlock data, then block 703 may be followed by block 707, "INTERRUPT ASSERTED IN PACKET?" If an interrupted is asserted in the received packet, then block 707 may be followed by block 709, "ASSERT INTERRUPT," where an interrupt may be asserted to a processor supported by the second computing device 103. Otherwise, block 707 may be followed by block 711, "ACCEPT PACKET DATA," where the second computing device 103, in response to the received and accepted data that is not associated with the interrupt or the interlock, may be configured to transmit corresponding data back to the first computing device 101 with a non time-sensitive approach.

To enhance the fault tolerance of the remote control system 100, in some embodiments, watchdog mechanisms may be employed in the node carrier board of the second computing device 103. For instance, one watchdog mechanism for the node carrier board may be configured to monitor whether interlock data expected to be received from the first computing device 101 is indeed received within a certain amount of time. If the watchdog times out, then a latcher error condition may occur, which may cause the node carrier board to transition into a safe state.

For non time-sensitive data transfer between the first computing device 101 and the second computing device 103, a pre-defined set of registers may be repeatedly looped, so that even if one packet is lost due to error, the packet may still reach its destination. The latency may correspond to the size of the data refresh area that the first computing device 101 and the second computing device 103 are configured to support. In one embodiment, this data refresh area may be defined by setting the start address and the end address of a buffer area.

For time-sensitive data transfer, time-sensitive registers may be memory mapped to a certain offset. Any register may be selected for time-sensitive data transfer even if it is outside or inside the data refresh area for the non time-sensitive data transfer. If there are more than two requestors for time-sensitive data transfer, an arbitration logic may be utilized.

Figure 8:
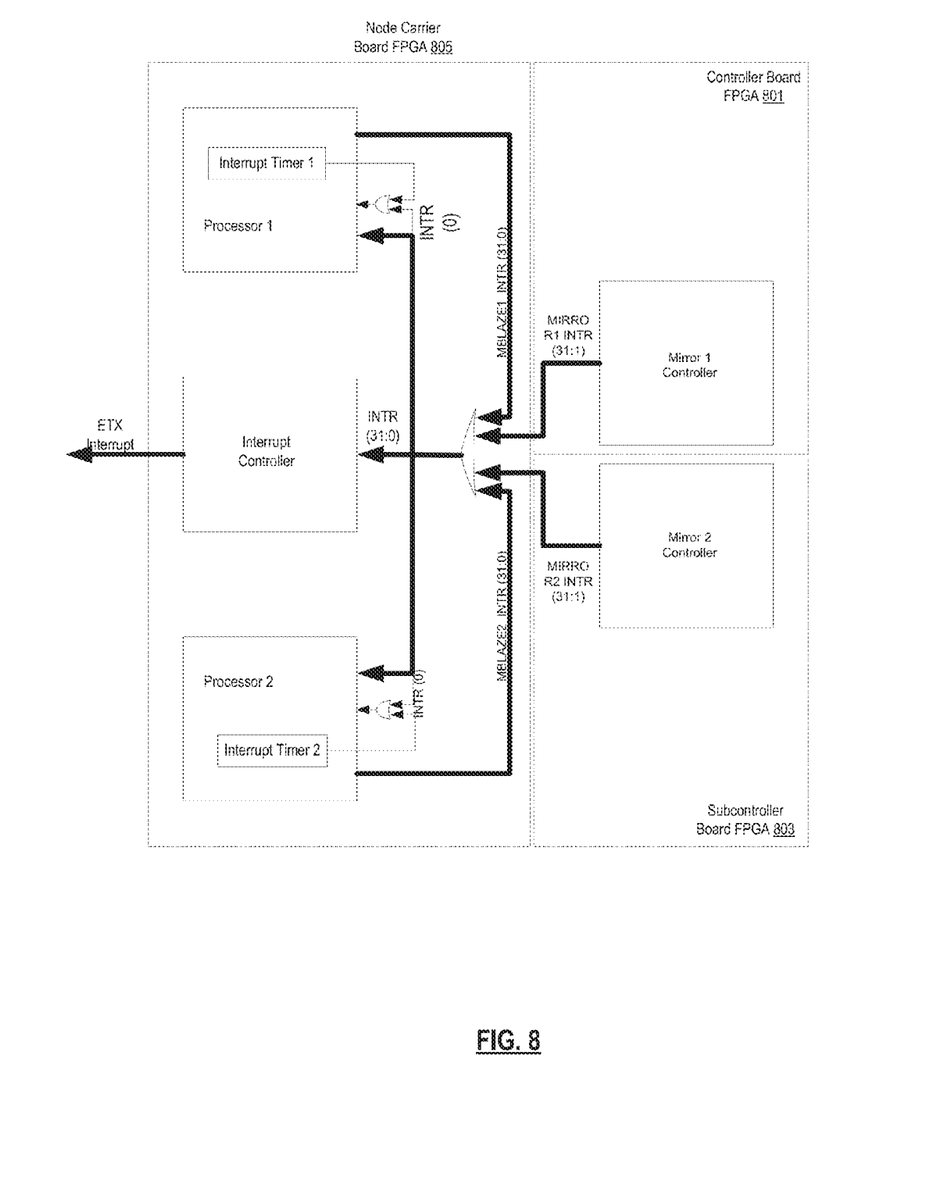
FIG. 8 is a block diagram illustrating one example interrupt flow, all arranged in accordance with at least some embodiments of the present disclosure.

FIG. 8 is a block diagram illustrating one example interrupt flow in accordance with one embodiment of the present disclosure. As shown, interrupt capability may be supported by a controller board FPGA 801 and a sub-controller board FPGA 803 on a controller board and a node carrier board FPGA 805 on a node carrier board. Multiple interrupts may be shared by a mirror 1 controller, a mirror 2 controller, a processor 1, and a processor 2. The mirror 1 controller and/or the mirror 2 controller may interrupt the processor 1, the processor 2, and ETX of the node carrier board. Similarly, the processor 1 or the processor 2 of the node carrier board may interrupt the ETX of the same node carrier board.

As shown, interrupts may be transferred to the node carrier board from the controller board FPGA 801 and the sub-controller board FPGA 803 as numbers. The interrupts may also be sent during normal packets (e.g., occupying certain bits of the packets). In some embodiments, limited interrupt information may be sent per packet (e.g., each packet may contain information associated with one interrupt). Some additional features of the interrupt capability may include, without limitation, 1) certain interrupt numbers may be pre-determined to be valid; 2) on the node carrier board, an interrupt bit corresponding to the interrupt number received may be set; 3) although it is not a requirement, a time-sensitive data transfer may be initiated and then the interrupt number may be provided on the read strobe (TX_MIRROR_RD_EN_COMB_OUT) of the critical cycle (TX_MIRROR_CRITICAL_CYCLE) by the FPGA logic at the same time the data is provided; 4) to address the possibility that interrupts may be missed on the node carrier board, the processor (e.g., ETX, microblaze, etc.) on the node carrier board may support a watchdog mechanism for interrupts that are raised from the controller board; 5) a built-in interrupt timer may be available for use per processor (e.g., microblaze) in the local register area associated with the processor. Writes of non-zero value may trigger the timer, cause the timer to count down, and then interrupt the processor; and 6) interrupt 0 may be raised by either the processor 1 or the processor 2. This interrupt may be shared with the interrupt timers (e.g., interrupt timer 1 and interrupt timer 2) associated with the processors, if such timers are enabled.

In some embodiments, the node board FPGA 805 may be configured to support an interlock controller (not shown in FIG. 8). In addition to the interlock controller, there may also be multiple interlock registers having multiple bits of interlock capability. There may be an override register associated with each of these interlock registers. Some of the interlock registers may be shared by the mirror 1 controller, mirror 2 controller, processor 1, and processor 2 of FIG. 8. The other interlock registers may be shared by the processor 1 and processor 2 of the node carrier board.

These interlock registers may also be programmed to have impact on a motion enable loop ("MEL"), which enables the moving of any axis which could collide with a patient, a power enable loop ("PEL"), which enables power required to support system functions, such as moving axes or beam, a beam enable loop ("BEL"), which enables radiation to be delivered, or kilo-volt BEL (KVBEL), which also enables radiation to be delivered. In some embodiments, these loops may correspond to physical current loops that are routed to most of the boards in a remote control system, such as the remote control system 100 of FIG. 1. For each loop, current may be sent out from a source and may be routed through all controller boards and then back to the source. Any controller board in the path of the loop may be configured to open or close its control switch in series with the loop. If all the control switches in series with a loop are closed, then current is allowed to flow and this may enable a function. Conversely, if any controller board in series with the loop opens its control switch, then current flow is prevented, and a function may be disabled.

The loop impact may be configured by the programming of the corresponding interlock register, such as the ILOCK_CONFIG register. For example, if bit 0 is set in an ILOCK_CONFIG register, that may be configured for PEL impact. If bit 1 is set in an ILOCK_CONFIG register, that may be configured for MEL impact. If bit 2 is set in an ILOCK_CONFIG register, that may be configured for BEL impact. If bit 3 is set in an ILOCK_CONFIG register, that may be configured for KVBEL impact.

The interlock controller may be configured to monitor interlock sources and latch them until the processor of the node carrier board, such as the ETX, clears them. Any asserted interlock in a loop's register may result in an open loop if interlock is not overridden. The node carrier board sometimes may override the interlock for debugging purposes.

To illustrate, suppose a controller board in the computing device 101 of FIG. 1 senses that a feedback encoder associated with motion in the treatment system 110 may have failed. In some embodiments, the controller board may be configured to assert the interlock that is dedicated to this particular feedback encoder and send the interlock in a special time-sensitive message to a node carrier board in the computing device 103. The interlock controller of the node carrier board would see the interlock data (e.g., by inspecting interlock registers) and inspect state information associated with the PEL, BEL, MEL, and KVBEL (e.g., the configuration bits). Given that this example is related to motion, the MEL bit would be set. Because the MEL bit is set, the node carrier board may be configured to send a MEL open control bit to the controller board, if the node carrier board has not overridden the interlock. Upon receiving the MEL open control bit, the controller board may be configured to open the MEL loop and thus disable motion on the treatment system 110 to prevent the failed feedback encoder from introducing improper motion.

In some embodiments, the communication control logic in the controller board may send interlock information from 4 interlock registers over 8 packets. The interlock information may be sent in the data field while sending time-sensitive packets with specific address. When an interlock signal is set in the controller board, the common control logic may increment the two bit interlock counter for that interlock by one (if previous interlock was already sent to the node carrier board) and wait for the turn to send interlock packet. The two-bit interlock counter may also help with mirrored architecture of the link and any missed interlock packet data. If any interlock packet was discarded due to error, the same information may be sent on the next available interlock packet.

The communication control logic may provide an option to specify time between transmissions of interlock data. The communication control logic may also provide generics for the controller board to indicate how many of the interlocks are being used. For example, a value of 0 may mean that interlock data is not sent to the node carrier board (two interlock packets are not sent). A value of less than 16 (interlock data in lower 16 bits of the register) may result in savings of one interlock packet. Lesser the number of interlock packets, better bandwidth utilization of the link (the time can be used for sending other packets).

On the node carrier board, an interlock may be accepted if the two-bit counter value is different from existing counter value. Otherwise, no interlock may be raised.

In some embodiments, the node carrier board FPGA 805 may be configured to support enable loop control logic, so that all of the aforementioned loops, PEL, BEL, MEL, and KVBEL, may be controlled by the node carrier board FPGA 805. The loop control logic may be configured to open the corresponding loop if any of the following conditions are met subject to the settings of the LOOP_IMPACT register of the other link: a) corresponding interlock is asserted, b) ETX loop control bit not set, c) processor 1 loop control bit not set, d) processor 2 loop control bit not set, e) communication error is asserted by Mirror 1 (Link 1), f) communication error is asserted by Mirror 2 (Link 2), g) ETX Watchdog timed-out, h) Processor 1 Watchdog timed-out, and g) Processor 2 Watchdog timed-out.

On the Controller board, PEL_CTRL, MEL_CTRL, BEL_CTRL and KVBEL_CTRL signals may be available from the common control logic to control the loops. These signals may be qualified with error signals on the controller board. The mirror 1 controller and mirror 2 controller may provide status of the loops back to the common control logic in the following ports—PEL_STAT, MEL_STAT, BEL_STAT and KVBEL_STAT.

In some embodiments, multiple watchdog mechanisms may be supported by the controller board and the node carrier board. Some example watchdog mechanisms supported on the node carrier board include, without limitation, a Peripheral Component Interconnect (PCI) watchdog, a processor (e.g., microblaze) watchdog, a node refresh watchdog, and a node interlock refresh watchdog. The PCI watchdog may be for the ETX of the node carrier board and may be hit within 22 mS. The microblaze watchdog may be hit within 1 mS. The node refresh watchdog may be configured to monitor the update times for the data sent from the controller board to the node carrier board. The address area to monitor and the timeout value may be programmed through register RX_CHECK_CONFIG. The node interlock refresh watchdog may be configured to monitor the update times for interlock data sent from the controller board to the node carrier board.

Some example watchdog mechanisms supported on the controller board include a controller refresh watchdog, which may be configured to monitor the update times for the data sent from the node carrier board to the controller board.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense.

We claim:

1. A system configured to support communication between a first environment having a first neutron radiation level and a second environment having a second neutron radiation level, comprising:
   a first computing device configured to control a treatment system in the first environment, wherein the treatment system collects a first radiation therapy time-sensitive data and a second radiation therapy non-time-sensitive data; and
   a second computing device configured to issue a command in the second environment for the treatment system, wherein the first computing device is further configured to:
   enable or disable a function supported by the treatment system based on the command from the second computing device,
   in response to the first radiation therapy time-sensitive data and the second radiation therapy non-time-sensitive data, assert a first interrupt or a first interlock based on the first radiation therapy time-sensitive data and transmit the first radiation therapy time-sensitive data with the first interrupt or the first interlock and a higher priority than the second radiation therapy non-time-sensitive data in a servo loop,
   retransmit the first radiation therapy time-sensitive data to the second computing device with the higher priority when the second computing device fails to receive expected information within a particular time, or when the first computing device receives a first monitored status of a first storage area in the first computing device, and
   retransmit the second radiation therapy non-time-sensitive data to the second computing device.

2. The system of claim 1, wherein the first computing device asserts the first interlock by setting interlock registers that the second computing device inspects, and the interlock registers are associated with at least a current loop routed to the system.

3. The system of claim 2, wherein the first computing device is further configured to receive an override command to open the current loop in response to the transmission of the first radiation therapy time-sensitive data and the first interlock.

4. The system of claim 3, in response to the override command or the control bit, wherein the first computing device is further configured to enable or disable the function.

5. The system of claim 1, wherein the first computing device is further configured to place the first radiation therapy time-sensitive data and the first interrupt in a time-sensitive packet before transmitting the packet.

6. The system of claim 1, wherein the first computing device is further configured to send a time-sensitive packet with an interrupt to request a resend of the command, if the first computing device fails to receive the command within a predetermined amount of time.

7. The system of claim 1, wherein the first environment is in close proximity with the second environment.

8. The system of claim 1, wherein the first computing device is further configured to retrieve the first radiation therapy time-sensitive data and the first interrupt or the first interlock from the first storage area, which corresponds to a first predetermined set of addresses designated to store time-sensitive data.

9. The system of claim 1, wherein a mirrored architecture is supported between the first computing device and the second computing device.

10. The system of claim 9, wherein the first computing device is further configured to periodically transmit data stored in a second storage area, which corresponds to a second predetermined set of addresses designated to store non-time-sensitive data in the second computing device.

11. The system of claim 10, wherein the first computing device is configured to retransmit the non-time-sensitive data to the second computing device when the first computing device receives a second monitored status of the second storage area.

12. The system of claim 1, wherein the first computing device is further configured to receive a retransmission request from the second computing device for the pending time-sensitive data if the second computing device fails to receive the pending time-sensitive data or the first interrupt within the particular time.

13. A system configured to support communication between a first environment having a first neutron radiation level and a second environment having a second neutron radiation level, comprising:
   a first computing device configured to control a treatment system in the first environment; and
   a second computing device configured to issue commands in the second environment for the treatment system, wherein
   the second computing device is further configured to:
   prior to responding to a first interrupt asserted by the first computing device based on a radiation therapy time-sensitive data, determine whether to issue a first command to the first computing device to enable or disable a first function supported by the treatment system in response to a first interlock asserted by the first computing device,
   if there is pending time-sensitive data to transmit, transmit the pending time-sensitive data with a higher priority than non-time-sensitive data, and
   perform a function in response to the first interrupt and based on the radiation therapy time-sensitive data from the first computing device,
   wherein the second computing device is further configured to:
   retransmit the pending time-sensitive data to the first computing device with the higher priority when the first computing device fails to receive expected information within a particular time, or when the second computing device receives a first monitored status of a first storage area in the second computing device; and
   retransmit the non-time-sensitive data to the first computing device.

14. The system of claim 13, wherein the second computing device is further configured to determine whether to issue the first command based on whether the first interlock is received from the first computing device within a predetermined period of time.

15. The system of claim 14, wherein the second computing device is further configured to inspect a predetermined register for the first interlock to determine whether the first interlock is received.

16. The system of claim 13, wherein the second computing device is further configured to transition to a safe state after the second computing device fails to receive the first interlock within a predetermined period of time.

17. The system of claim 13, wherein the first environment is in close proximity with the second environment.

18. The system of claim 13, wherein the second computing device is further configured to retrieve the time-sensitive data from the first storage area, which corresponds to a first predetermined set of addresses designed to store time-sensitive data in the second computing device.

19. The system of claim 13, wherein a mirrored architecture is supported between the first computing device and the second computing device.

20. The system of claim 19, wherein the second computing device is further configured to periodically transmit data stored in a second storage area, which corresponds to a second predetermined set of addresses designated to store non-time-sensitive data in the second computing device.

21. The system of claim 20, wherein the second computing device is configured to retransmit the non-time-sensitive data to the first computing device when the second computing device receives a second monitored status of the second storage area.

22. The system of claim 13, wherein the second computing device is further configured to receive a retransmission request from the first computing device for the pending time-sensitive data if the first computing device fails to receive the pending time-sensitive data or the first interrupt within the particular time.

* * * * *